US012246182B2

(12) United States Patent
Martens et al.

(10) Patent No.: US 12,246,182 B2
(45) Date of Patent: Mar. 11, 2025

(54) IMPLANTABLE RESTRAINT AND STIMULATION DEVICE CONFIGURED FOR EXPLANTATION

(71) Applicant: SALVIA BIOELECTRONICS B.V., Eindhoven (NL)

(72) Inventors: Hubert Martens, Eindhoven (NL); Daniel Schobben, Eindhoven (NL)

(73) Assignee: SALVIA BIOELECTRONICS B.V., Eindhoven (NL)

( * ) Notice: Subject to any disclaimer, the term of this patent is extended or adjusted under 35 U.S.C. 154(b) by 722 days.

(21) Appl. No.: 17/430,299

(22) PCT Filed: Feb. 10, 2020

(86) PCT No.: PCT/IB2020/051034
§ 371 (c)(1),
(2) Date: Aug. 11, 2021

(87) PCT Pub. No.: WO2020/165735
PCT Pub. Date: Aug. 20, 2020

(65) Prior Publication Data
US 2022/0193428 A1 Jun. 23, 2022

(30) Foreign Application Priority Data
Feb. 11, 2019 (NL) .................................... 2022555

(51) Int. Cl.
*A61N 1/375* (2006.01)
*A61N 1/05* (2006.01)
(52) U.S. Cl.
CPC ....... *A61N 1/37518* (2017.08); *A61N 1/0558* (2013.01)
(58) Field of Classification Search
CPC .............. A61N 1/37518; A61N 1/0558; A61N 1/3605; A61N 1/36075
See application file for complete search history.

(56) References Cited

U.S. PATENT DOCUMENTS 5,807,399 A * 9/1998 Laske .................... A61N 1/057
606/108
8,244,377 B1 8/2012 Pianca
(Continued)

FOREIGN PATENT DOCUMENTS

DE 102004035903 A 2/2006
WO 2004021870 A2 3/2004
WO 2010107751 A2 9/2010

OTHER PUBLICATIONS

Search Report for International Patent Application PCT/IB2020/051034, mailed on May 6, 2020.

*Primary Examiner* — Eugene T Wu
(74) *Attorney, Agent, or Firm* — Fresh IP PLC; Clifford D. Hyra; Aubrey Y. Chen

(57) ABSTRACT

An implantable restraint is provided that includes an opening-configured to receive a tissue anchor; a pair of protrusions between the opening and a distal edge, providing an anchor resistance to a longitudinal force; where the pair of protrusions are further configured to separate by a distance approximately equal to the tissue anchor when the longitudinal force exceeds a first predetermined threshold, such that the pair of protrusions moves past the tissue anchor.

By providing one or more openings extending through the substrate, the growth of tissue which naturally occurs after implantation is utilized to assist in securing the implantable restraint at the implantation site. By providing the pair of protrusions configured to provide resistance, a high degree of control of the restraining force and the explantation force is provided.

22 Claims, 10 Drawing Sheets

(56) References Cited

U.S. PATENT DOCUMENTS

| | | |
|---|---|---|
| 2003/0233139 A1 | 12/2003 | Chitre |
| 2006/0020317 A1 | 1/2006 | Flach |
| 2007/0100414 A1 | 5/2007 | Licata |
| 2011/0046437 A1 | 2/2011 | Kassab |
| 2011/0106247 A1 | 5/2011 | Miller |
| 2012/0150272 A1 | 6/2012 | Melsheimer |
| 2014/0277461 A1 | 9/2014 | Nebosky |
| 2016/0279411 A1 | 9/2016 | Rooney et al. |
| 2017/0312501 A1* | 11/2017 | Bornzin ............... A61N 1/0587 |
| 2017/0348522 A1 | 12/2017 | Stoffregen et al. |
| 2018/0325644 A1 | 11/2018 | Felix |

* cited by examiner

IMPLANTABLE RESTRAINT AND
STIMULATION DEVICE CONFIGURED FOR
EXPLANTATION

FIELD

The present disclosure relates to an implantable restraint configured for explantation. In particular, it relates to an implantable stimulation device, such as for neurostimulation, configured for explantation.

BACKGROUND

Implantable stimulation systems may be used to deliver electrical stimulation therapy to patients to treat a variety of symptoms or conditions such as headaches, lower back pain and incontinence.

In many electrical stimulation applications, it is desirable for a stimulation device, typically comprising a medical lead, to resist migration following implantation. For example, it may be desirable for one or more electrodes disposed at a distal end of the implantable medical lead to remain proximate to a target stimulation site in order to provide adequate and reliable stimulation of the target stimulation site. In some applications, it may also be desirable for the electrodes to remain substantially fixed in order to maintain a minimum distance between an electrode and a nerve. Securing the implantable medical lead at the target stimulation site may minimize lead migration.

Conventional implantable medical leads, such as described in U.S. Pat. No. 8,244,377, comprise one or more restraints in the form of barbs to reduce the risk of lead migration. However, these barbs make it more difficult to explant (remove) the medical lead, complicating the surgical procedure. In addition, the barbs increase the volume occupied by the lead—in particular, for implants just under the skin, the patient may be able to feel the restraints through the skin. This may lead to reduced comfort, and often results in the lead protrusions piercing through the skin. In some cases, during explantation, the barbs may even break off, making their removal even more difficult.

Similar problems occur with other kinds of implants which preferably have a low degree of migration, such as those providing delivery of a substance, such as a pharmaceutical composition, to a particular anatomical location. If the treatment by the implant is temporary or the implant needs to be replaced, explantation may require extensive surgery as described above for implantable leads. For example, with a birth control implant, explantation must be performed when the dosage is no longer effective, or the person wishes to stop the treatment. In some cases, this may be several years after implantation—it is very inconvenient if the implant has migrated substantially. Typically, some form of anchor or restraint will be used to keep the implants in place—however, with traditional restraints, they may become encased in tissue. As above, they may also break off during explantation, or make the procedure to remove all the parts of the implant much more complicated.

US patent application US 2016/0279411A1 describes delivery of peripheral nerve field stimulation (PNFS) in combination with one or more other therapies. A paddle lead is described with fixation structures.

US patent application US 2003/0233139A1 describes an implantable cardiac stimulation lead system for use with an implantable stimulation device. It comprises an insulating sheath, formed with a passive fixation feature formed into the outer peripheral surface for encouraging tissue ingrowth.

DE patent application DE 102004035903A, and its family member US 2006/0020317 A1, describes fixings for implantable electrodes and catheters.

US patent application US 2017/0348522A1 describes an electrical stimulation lead, comprising a paddle body and an anchoring device, threadably disposed in at least a portion of the paddle body.

US patent application US 2014/0277461A1 describes a three-dimensional scaffold for a medical implant including a plurality of layers bonded to each other. Each layer has a top surface and a bottom surface and a plurality of pores extending from the top surface to the bottom surface.

WO patent application WO 2004/021870A2 describes devices, systems and methods employing magnetic force to resist tissue collapse in targeted pharyngeal structures and individual anatomic components within the pharyngeal conduit during sleep.

It is an object of the invention to provide an improved implantable restraints that provides a high resistance to migration, and also provides a low degree of resistance to explantation.

General Statements

According to a first aspect of the present disclosure, there is provided an implantable restraint comprising: an elongated substrate, disposed along a longitudinal axis, the substrate having a first and second surface disposed along transverse planes, the substrate further comprising: an opening, substantially reducing the substrate thickness between the first and second surface, configured to receive in-growth of human or animal tissue after implantation such that a tissue anchor may form; a pair of protrusions, disposed between the opening and a distal edge of the substrate, the protrusions being configured to provide an anchor resistance against the tissue anchor to a longitudinal force applied to a proximal section of the substrate; wherein the pair of protrusions are further configured to separate by a distance approximately equal to a transverse extent of the tissue anchor when the longitudinal force exceeds a first predetermined threshold, such that the pair of protrusions moves past the tissue anchor in the direction of the longitudinal force.

By providing one or more openings substantially reducing the thickness of the substrate, the growth of tissue which naturally occurs after implantation is utilized to assist in securing the implantable restraint at the implantation site. By providing the pair of protrusions configured to provide resistance, a high degree of control of the restraining force and the explantation force is provided. Protrusions attached and/or integrated into the elongated substrate lie flatter, reducing the thickness of the implantable restraint, and reducing the need for other types of anchors and sutures.

Optionally, the opening extends through the substrate between the first and second surface. This may provide a higher degree of tissue growth, and a higher degree of securing. This may be particularly advantageous when the substrate is relatively thin. Optionally, the first and second surfaces are disposed along substantially parallel transverse planes. This may simplify the predetermination of one or more force thresholds.

According to a second aspect of the present disclosure, there is provided an implantable restraint wherein the pair of protrusions face each other.

By configuring the protrusions to be substantially symmetrical at the outer extent, they co-operate as a pair so that the retaining force and explantation force may be tuned by modifying the physical properties of the materials used.

providing for symmetrical protrusions and/or a symmetrical opening which may provide a more predictable force threshold for explantation.

According to another aspect of the present disclosure, there is provided an implantable restraint which further comprises a distal opening, substantially reducing the thickness of the substrate, and disposed between the pair of protrusions. Optionally, the distal opening extends through the substrate.

By including a distal opening, the risk that pieces of the implantable restraint are left behind after explantation may be greatly reduced.

According to a further aspect of the present disclosure, there is provided an implantable restraint comprising a region, disposed between the pair of protrusions, configured to provide a separation resistance against an increase in the separation distance of the pair of protrusions; wherein the region is further configured to rupture when the longitudinal force exceeds a second predetermined threshold, such that a distal opening is disposed between the pair of protrusions.

By providing predetermining rupture points, the implantable restraint may be explanted by applying a predetermined longitudinal force, while greatly reducing the risk that material from the restraint, and in particular substrate material, is left behind at the implantation site.

In another aspect of the invention, an implantable restraint is provided wherein the region, configured to provide a separation resistance, is contiguous.

The use of any additional materials or additional parts, even when firmly attached to the substrate by gluing or welding, increases the risk of material being left behind after explantation. By ensuring that the region is contiguous, such risks may be greatly reduced. Note that the physical properties in the region may be different to the physical properties of the surrounding substrate, even when contiguous.

Alternatively or additionally, the region and/or protrusions may further comprise one or more coatings, filaments and/or wires, or any combination thereof, configured and arranged to increase the resistance of the protrusions to separate.

Alternatively or additionally, the region and/or protrusions may further comprise one or more depressions, indentations, reductions in thickness, perforations, serrations, holes, or any combination thereof, configured and arranged to at least partially predetermine the resistance of the protrusions to separate.

In a further aspect of the invention, the implantable restraint may be configured and arranged such that the first predetermined threshold and/or second predetermined threshold is in the range 0.1 to 10 Newtons (N). Alternatively, the first predetermined threshold and/or second predetermined threshold is in the range 0.5 N to 2N. Alternatively, the first predetermined threshold and/or second predetermined threshold is approximately 1 N.

These ranges and values provide a preferred region of operation, allowing removal of the implant with a reasonable degree of force, while ensuring that the implantable restraint remains relatively fixed during patient movement and any patient interaction required with the implantable restraint.

In still another aspect of the invention, an implantable stimulation device is provided comprising: an elongated substrate; one or more stimulating electrodes, configured to transmit energy to human or animal tissue during use; one or more implantable restraints according to any of the preceding claims, the restraints being attached and/or integrated into the elongated substrate.

BRIEF DESCRIPTION OF THE DRAWINGS

Features and advantages of some embodiments of the present invention, and the manner in which the same are accomplished, will become more readily apparent upon consideration of the following detailed description of the invention taken in conjunction with the accompanying drawings, which illustrate preferred and exemplary embodiments, and which are not necessarily drawn to scale, wherein.

DETAILED DESCRIPTION

In the following detailed description, numerous non-limiting specific details are given to assist in understanding this disclosure.

Figure 1A:
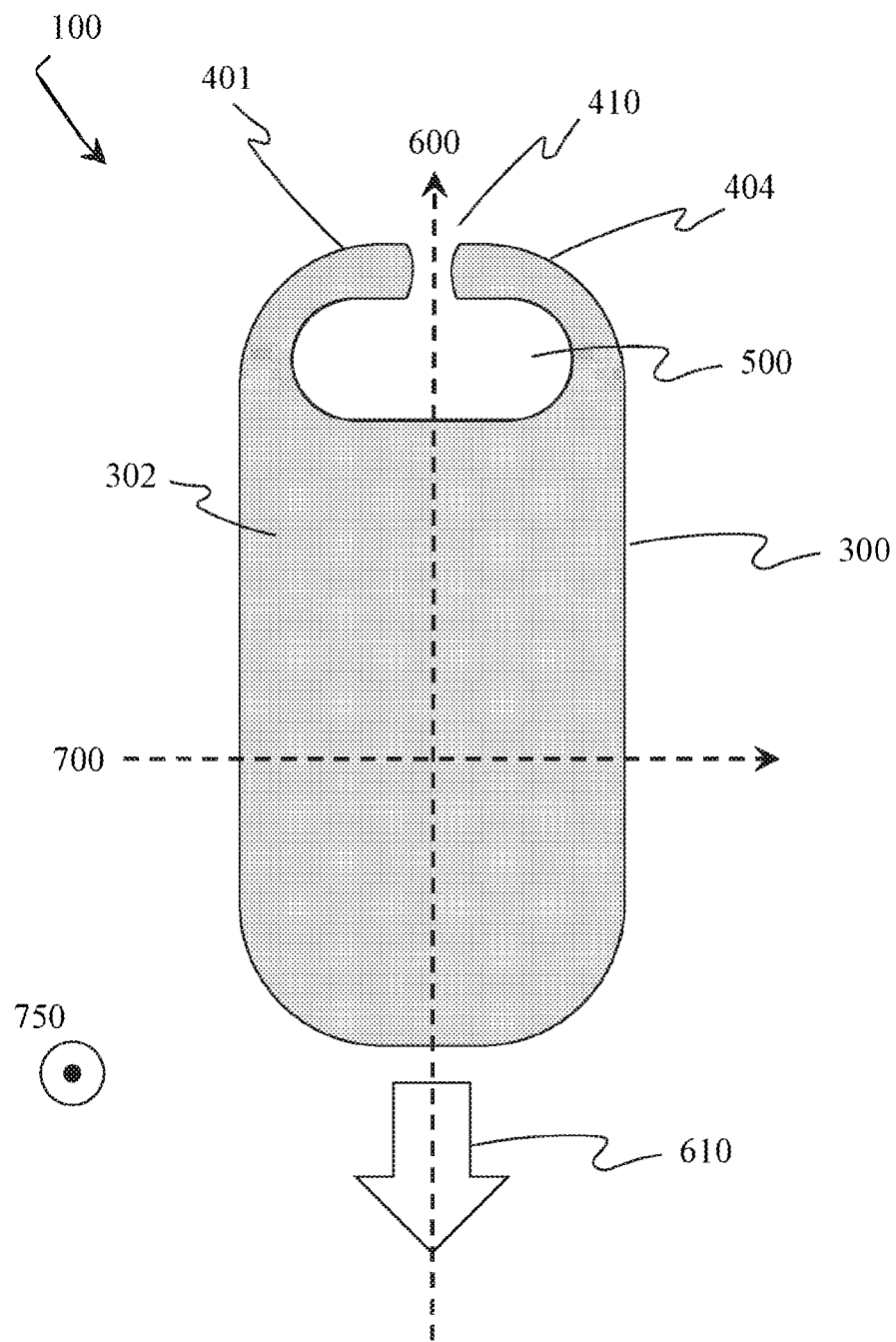
FIGS. 1A and 1B depict a first example of an implantable restraint.

FIG. 1A depicts an implantable restraint 100 comprising:
an elongated substrate 300, disposed along a longitudinal axis 600, the substrate having a first 302 and second 303 surface disposed along substantially parallel transverse planes 600, 700. As depicted, the first surface 302 is the visible top surface, lying in the plane comprising the longitudinal axis 600 and a first transverse axis 700—the first transverse axis 700 is substantially perpendicular to the longitudinal axis 700. As depicted, this is substantially parallel to the plane of the drawing (the surface of the paper). The substrate 300 has a thickness or extent along a second transverse axis 750—this second transverse axis 750 is substantially perpendicular to both the longitudinal axis 600 and the first transverse axis 700—it is substantially perpendicular to the plane of the drawing as depicted.

As the substrate 300 may be relatively thin with a degree of flexibility, the degree to which the transverse planes 600, 700 are parallel may be determined by positioning the substrate 300 on a substantially flat service.

The substrate 300 may have any suitable cross-section profile. Having the surfaces 302, 303/transverse planes 600, 700 substantially parallel is not essential, but it is preferred as it may simplify the predetermination of the thresholds explained below for many embodiments.

To clarify the different views of the implantable restraint, the axes are given nominal directions:
the longitudinal axis 600 extends from the proximal end of the restraint, depicted at the bottom of the page, to the distal end, depicted at the top of the page;
the first transverse axis 700 extends from left to right as depicted on the page, when the first surface 302 is viewed from above; and the second transverse axis 750 extends out of the pages as depicted.

The second surface 303 is not depicted in FIG. 1A, but lies at a lower position along the second transverse axis 750, and is also substantially parallel to the plane of the drawing.

As the substrate 300 may be relatively thin with a degree of flexibility, the degree to which the surfaces 302, 303 are parallel may be determined by positioning the substrate 300 on a substantially flat service.

The substrate 300 further comprises:

an opening 500, substantially extending through the substrate 300, along the second transverse axis 750, between the first 302 and second 303 surfaces. This opening is configured to receive in-growth of human or animal tissue after implantation such that a tissue anchor may form. More than one such opening 500 may be used to anchor the restraint 100. The opening 500 may also be an aperture—the form and dimensions of the opening 500 are predetermined to provide a certain degree of fixation at a tissue location where the implant 100 is to be restrained. After implantation, the human or animal body will naturally generate tissue at the implantation site—this will enter the opening 500, creating a strong attachment to the restraint 100 at the location of the opening 500. This may also be called bio-connecting, tissue locking or tissue in-growth.

Figure 8:
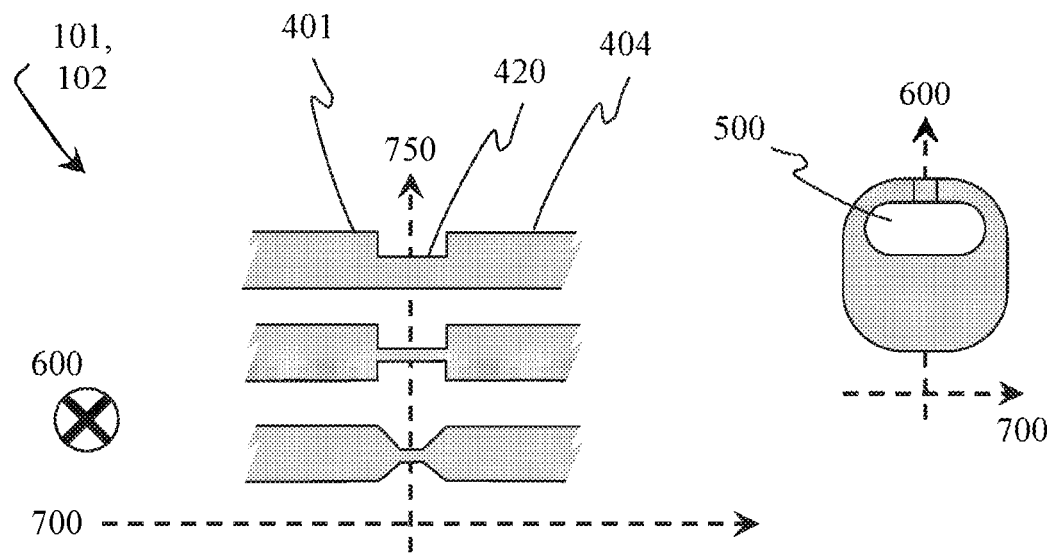
FIG. 8 depicts modifications of the thickness of the separation resistance region of an implantable stimulation device.

In general, indentations may be used instead of holes, or in combination with holes. In addition, the thickness (extent along the second transverse axis 750) may also be modified, as depicted in FIG. 8 (see below). The reduction in thickness may be comprised in the first surface 302, in the second surface 303, or in both.

The substrate 300 also comprises:

a pair of protrusions 401, 404, disposed between the opening 500 and a distal edge of the substrate 300, the protrusions 401, 404 being configured to provide a first resistance against the tissue anchor to a longitudinal force 610 applied to a proximal section of the substrate 300. As depicted, the longitudinal force 610 is applied in a negative direction along the longitudinal axis 600, which is downwards. It is this first resistance which provides a degree of restraint against migration due to a longitudinal force. The transverse edges along the first transverse axis 700 provide a degree of restraint against migration due to a transverse force.

The pair of protrusions 401, 404 are further configured to separate by a distance approximately equal to a transverse extent 700 of the tissue anchor when the longitudinal force 610 exceeds a first predetermined threshold, such that the pair of protrusions 401, 404 moves past the tissue anchor in the direction of the longitudinal force 610.

One of the insights on which the invention is based is that the natural growth of tissue which occurs after implantation may be utilized to secure the implantable device at the implantation site. This natural growth is currently considered an annoyance as it makes explantation more difficult—in some cases surgery may even be required to remove implantable electrode leads.

By providing one or more openings 500 extending through the substrate 300, the sites at which tissue growth occurs are at least partially predetermined, and preferably predetermined to a high degree. The extent of the one or more openings 500 along the transverse axis 700 and along the longitudinal axis 600 are factors which influence the degree of tissue growth which may occur, and also influence the degree by which the restraint 100 is fixed in the section proximate the opening 500.

Figure 1B:
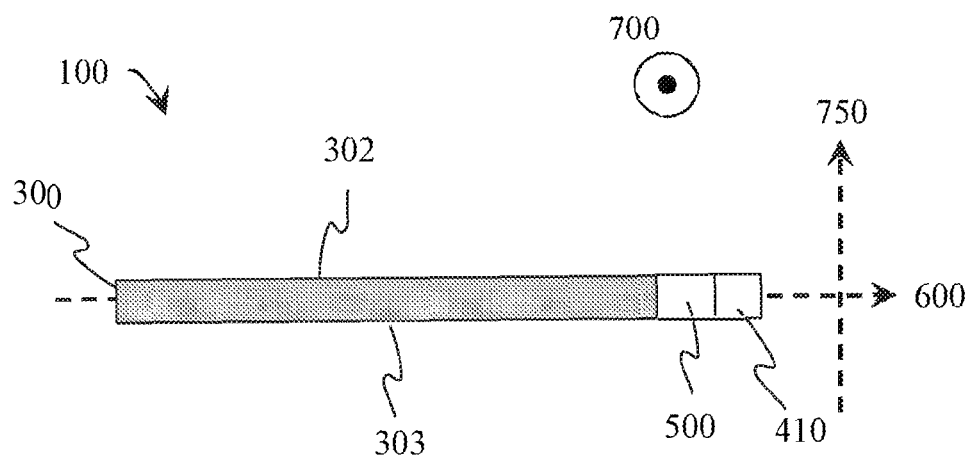

FIG. 1B shows a transverse cross section of the implantable restraint 100 depicted in FIG. 1A. It is depicted in the plane comprising the longitudinal axis 600 and the second transverse axis 750, with the longitudinal axis 600 depicted from left to right, and the second transverse axis 750 is depicted from bottom to top. Both the first 302 and second 303 surfaces are depicted as respectively an upper and lower surface. The opening 500 substantially extends through the substrate 300 between the first 302 and second surface 303.

In this embodiment 100, there is a distal opening 410 between the protrusions 401, 404, substantially extending through the substrate—in other words, there is a separation distance between the pair of protrusions 401, 404 across the transverse extent 700 of the distal opening 410. In terms of the invention, the distal opening 410 provides substantially zero resistance against an increase of the separation distance of the pair of protrusions 401, 404. Depending on the transverse 700 and longitudinal 600 extent of the distal opening 410, some tissue in-growth may occur in the distal opening 410 providing a relatively small resistance against an increase in the protrusion pair 401, 404 separation distance.

As described below, indentations may be used instead of substantially extending through. In addition, the thickness (extent along the second transverse axis 750) may also be modified, as depicted in FIG. 8 (see below). The reduction in thickness may be comprised in the first surface 302, in the second surface 303, or in both The restraint 100 is configured and arranged such that when a longitudinal force 610 above a predetermined threshold is applied to a proximal end, the pair of protrusions 401,404 separate by a distance approximately equal to a transverse extent 700 of the tissue anchor, such that the pair of protrusions 40, 404 moves past the tissue anchor in the direction of the longitudinal force 610.

In general, this predetermined threshold may include one or more of the following contributions:
a) a resistance of the distal edge of the opening 500 against any tissue anchor which has in-grown in the opening 500 after implantation;
b) a resistance of the protrusion pair 401, 404 against any tissue anchor in the opening 500 due to the physical form and properties of the protrusions 401, 404;
c) a resistance against an increase in the separation distance of the pair of protrusions 401, 404 due to any further tissue anchor which has in-grown in the distal opening 410 after implantation;
d) a resistance against an increase in the separation distance of the pair of protrusions 401, 404 due to the physical form and properties of the protrusions 401, 404; and
e) a resistance against an increase in the separation distance of the pair of protrusions 401, 404 due to the physical form and properties of the region between the pair of protrusions 401, 404. As mentioned above, in this embodiment of the restraint 100, this resistance is substantially zero due to the region being a distal opening 410. In the other embodiments discussed below, this region contributes a more than zero resistance.

a) and b) are referred to as anchor resistance; and c), d) and e) are referred to as separation resistance. Both types of resistance must be overcome before the implantable restraint can be explanted The resistance of the protrusion pair 401, 404 against any tissue anchor in the opening 500 may be determined by using a particular physical form and/or changing/selecting the physical (and material) properties of the protrusions 401, 404.

One of the basic parameters to determine the anchor resistance are the physical dimensions of the protrusion pair 401, 404—the thickness (extent along second transverse axis 750), the width (extent along the longitudinal axis 600), the protrusion "arm" length (extent along the first transverse axis 700) and the curvature of the "arms". In addition, the materials used to form the protrusions 401, 404 also influence the anchor resistance due to parameters such as:

Young's Modulus of the material
the thickness of the individual material layers
the number of layers from which the material stack is composed
any metal tracks that are included into the material stack, which increases the stiffness of the protrusions.

For example, the elongated substrate 300 may comprise an elastomeric distal end composed of silicone rubber, or another biocompatible, durable polymer such as siloxane polymers, polydimethylsiloxanes, polyurethane, polyether urethane, polyetherurethane urea, polyesterurethane, polyamide, polycarbonate, polyester, polypropylene, polyethylene, polystyrene, polyvinyl chloride, polytetrafluoroethylene, polysulfone, cellulose acetate, polymethylmethacrylate, polyethylene, and polyvinylacetate. The pair of protrusions 401, 404 may comprise one or more compounds and/or substances comprised in the substrate 300, or something different. Suitable examples of polymers, including LCP, are described in "Polymers for Neural Implants", Hassler, Boretius, Stieglitz, Journal of Polymer Science: Part B Polymer Physics, 2011, 49, 18-33 (DOI 10.1002/polb.22169), In particular, Table 1 is included here as reference, depicting the properties of Polyimide (UBE U-Varnish-S), Parylene C (PCS Parylene C), PDMS (NuSil MED-1000), SU-8 (MicroChem SU-8 2000 & 3000 Series), and LCP (Vectra MT1300).

Flexible substrates 300 are also preferred as they follow the contours of the underlying anatomical features very closely. Very thin substrates 300 have the additional advantage that they have increased flexibility.

Preferably, the flexible substrate 300 comprises a Liquid Crystal Polymer (LCP), Parylene and/or a Polyimide. Liquid Crystal Polymers (LCP) are chemically and biologically stable thermoplastic polymers which allow for hermetic sensor modules having a small size and low moisture penetration.

Advantageously, LCP may be thermoformed allowing complex shapes to be provided. Very thin and very flat sections of LCP may be provided, allowing a wide range of protrusion pair 401, 404 sizes and shapes to be provided. For fine tuning, a suitable laser may also be used for cutting and the distal end may be flattened to a higher degree than the rest of the substrate. For example, LCP substrates 300 with thicknesses (extent along the second transverse axis 750) in the range 50 microns (μm) to 700 microns (μm) may be used, preferably 100 microns (μm) to 300 microns (μm). For example, values of 150 μm (micron), 100 μm, 50 μm, or 25 μm may be provided. Similarly, protrusion widths (extent along the longitudinal axis 600) of 150 μm, 100 μm, 50 μm or 25 μm may be provided using LCP, for example.

At room temperature, thin LCP films have mechanical properties similar to steel. This is important as implantable substrates 300 must be strong enough to be implanted, strong enough to be removed (explanted) and strong enough to follow any movement of the anatomical feature and/or structure against which it is implanted.

LCP belongs to the polymer materials with the lowest permeability for gases and water. LCP can be bonded to itself, allowing multilayer constructions with a homogenous structure.

In contrast to LCP, Polyimides are thermoset polymers, which require adhesives for the construction of multilayer substrates. Polyimides are thermoset polymer material with high temperature and flexural endurance.

LCP may be used, for example, to provide a substrate having multilayers (not depicted)—in other words, several layers of 25 μm (micron) thickness. Electrical interconnect layers may also be provided by metallization using techniques from the PCB industry, such as metallization with a bio-compatible metal such as gold or platinum. Electroplating may be used. These electrical interconnect layers may be used to provide electrical energy to any electrodes.

For example, LCP materials are available from Zeus Industrial Products (www.zeosinc.com/lp/technical-papers/lpc-introduction-to-liquid-crystal-polymers), Typical physical properties from Zeus are:

|  | ASTM | LCP |
|---|---|---|
| PHYSICAL |  |  |
| Density (g/cc) | D792 | 1.40-1.51 |
| Water Absorption (%) | D570 | 0.003-0.006 |
| Refraction Index |  | N/A |
| MECHANICAL |  |  |
| Tensile/Young's Modulus (MPa) | D638 | 10,000-37,900 |
| Tensile Stress/Strength (MPa) | D638 | 44.8 to 100 |
| Elongation at Break (%) | D638 | 0.40-5.8 |
| Flexural Modulus (MPa) | D790 | 7,580-19,300 |
| Flexural Strength (MPa) | D790 | 68.6 to 159 |
| ELECTRICAL |  |  |
| Volume Resistivity (Ω-cm) | D257 | $4 \times 10^{14}$ |
| Relative Permittivity | IEC 60250 | 4.39 |
| Dissipation Factor | D149 | $1.0^{-3}$ to 0.035 |
| THERMAL |  |  |
| Load (° C.) | D648 | 232-293 |
| Maximum Service Temp, Air (° C.) |  | 150 |
| Minimum Service Temp, Air (° C.) |  | −50 |
| Melt Temp (° C.) |  | 280-330 |
| Coefficient of Thermal Expansion, linear 20° (μm/m-° C.) | D696 | 0-0.05 |

As a longitudinal force 610 is applied, the protrusion pair 401, 404 provide a degree of anchor resistance. When the longitudinal force 610 exceeds a first predetermined threshold, the arms of the protrusions 401, 404 start to bend and/or twist, such that they open to a sufficient degree that the arms of the protrusions 401, 404 pass around the tissue anchor as the implantable restraint 100 is explanted.

The force to be applied to remove the restraint 100 may predetermined to be in the range 0.1 Newton (N) to 10 N. Alternatively, the force may predetermined to be in the range 0.5 N to 2N. Alternatively, the force may predetermined to be in approximately 1 N.

The pair of protrusions 401, 404 may substantially face each other, providing for symmetrical protrusions and/or a symmetrical opening 500 which may provide a more predictable force threshold for explantation.

Preferably, a low aspect ratio is used for the elongated substrate to reduce the chance of implantation problems—for example a ratio of height (thickness or extent along the second transverse axis 750) to width (extent along the first transverse axis 700) of less than 10, such as 0.3 mm high and 10 mm wide(=ratio 1:33).

One of the insights on which the invention is based is that such low aspect ratio substrates allow openings 500 to be provided which substantially extend through the entire thickness, promoting tissue in-growth at these locations.

In addition, the implantable restraint 100 uses fixing protrusions in approximately the same plane as the substrate 300. This reduces the likelihood that the restraints will be felt by the patient through the skin, and the possibility that the protrusions would pierce the skin is greatly reduced. In addition, the restraint 100 uses protrusions rigidly attached and/or integrated into the substrate 300, preferably comprising the same material(s) as the substrate 300. This reduces the need for additional anchors and/or sutures.

Alternatively a substrate may be used with a substantially circular (which includes a circle, a flattened circle, a stadium, an oval and an ellipse) transverse cross-section—this may also be described as tubular or cylindrical.

Although only one opening 500 is depicted, the skilled person will realize that the restraint 100 may comprise a plurality of openings 500 and a plurality of corresponding protrusions 401, 404—the implantable restraint 100 may be fixed at a plurality of points along the length of the substrate 300.

In general, each opening 500 is substantially predetermined to secure the implantable device 101 (medical lead) at the implantation site. Parameters that determine the degree of positional security include:

the position of the one or more openings 500. In other words, the environment proximate the opening 500 after implantation may influence the extent and rate of tissue growth.

the number and distribution of the one or more openings 500. More openings provide, in general, more locations for tissue to grow. The distribution may determine the degree to which a section of the restraint 100 is fixed. For example, one or more openings 500 with a small pitch (close together) may be used proximate any stimulation electrodes because these generally require a higher degree of positional security. In many case, stimulating electrodes are disposed proximate the distal end (a preferred location for an opening 500) to keep the extent of the implanted lead as short as possible.

the transverse 700 and/or longitudinal extent 600 of the one or more openings 500. In general, it is expected that a larger opening will provide for a higher extent of in-growth, which is expected to increase positional security.

the thickness of the substrate 300 or distance between the first surface 302 and the second surface 303. In general, a stronger positional security may be achieved if the tissue growth passes all the way through the substrate 300. A further insight upon which the invention is based is that the emergence of newer bio-compatible substrate materials with a higher tensile strength means that thinner substrates 300 may be used, increasing the chance that tissue growth can pass the whole way through.

the human or animal tissue against which the implantable restraint 100, is implanted. The rate and extent of tissue growth may also depend on the individual patient and the implantation site.

Typically, the openings 500 will have a minimum extent of 1 mm, with a preferred extent along at least one axis of 5 mm. The selected dimensions depend on the rate of tissue growth to be expected at the implant location in the body.

Figure 1C:
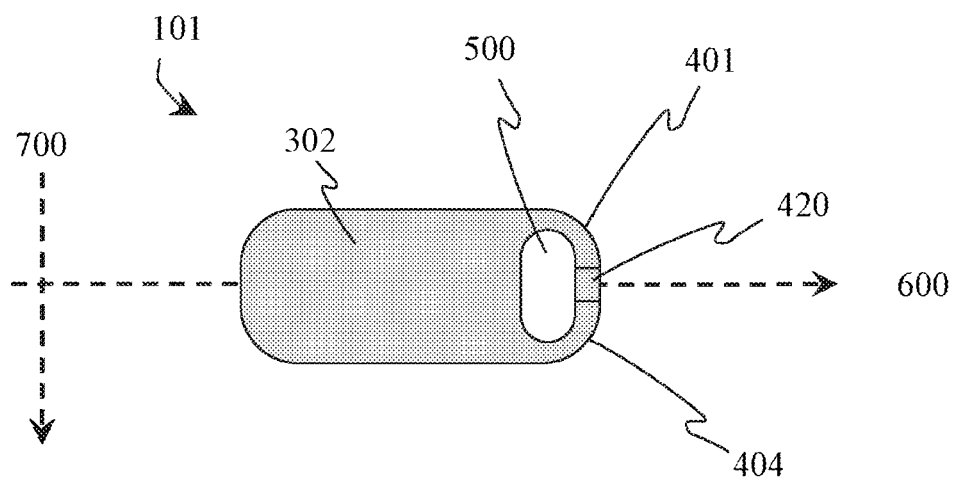
FIGS. 1C and 1D depict a second example of an implantable restraint.

FIG. 1C depicts a modified implantable restraint 101—it is similar to the implantable restraint 100 described in relation to FIGS. 1A and 1B, except for comprising:

a region 420, disposed between the pair of protrusions 401, 404, configured to provide a separation resistance against an increase in the separation distance of the pair of protrusions 401, 404, wherein the region 420 is further configured to rupture when the longitudinal force 610 exceeds a second predetermined threshold, such that a distal opening 410 is disposed between the pair of protrusions 401, 404. In other words, the pair of protrusions 401, 404 are connected together, and after the connection has ruptured, the pair of protrusions are no longer connected together and the restraint 101 then resemble the earlier depicted restraint 100.

Figure 1D:
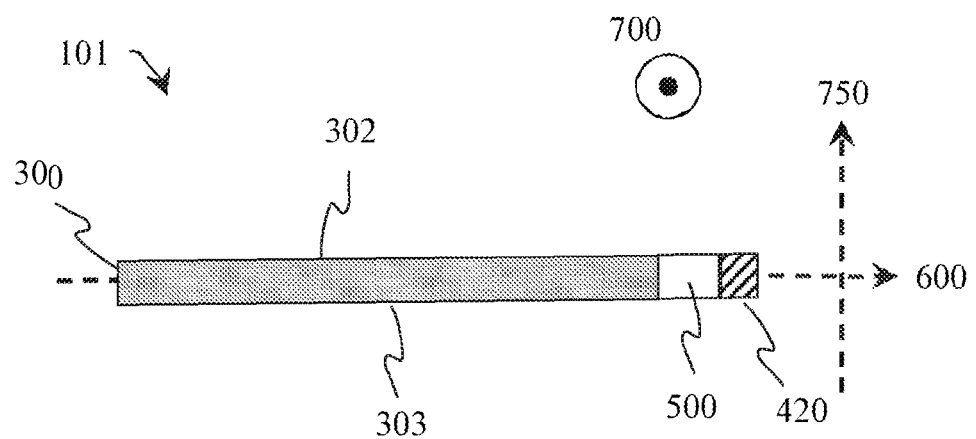

FIG. 1D shows a transverse cross section of the implantable restraint 101 depicted in FIG. 1C. It is depicted in the plane comprising the longitudinal axis 600 and the second transverse axis 750, with the longitudinal axis 600 depicted from left to right, and the second transverse axis 750 is depicted from bottom to top. Both the first 302 and second 303 surfaces are depicted as respectively an upper and lower surface. The opening 500 substantially extends through the substrate 300 between the first 302 and second surface 303.

In this embodiment 101, there is a region 420 between the protrusions 401, 404—in other words, there is a separation distance between the pair of protrusions 401, 404 across the transverse extent 700 of the region 420. In terms of the invention, the region 420 provides a (separation) resistance against an increase of the separation distance of the pair of protrusions 401, 404.

By providing one or more respective regions of configured separation resistance 420, rupture points are provided allowing the restraint to be explanted by applying a suitable and, to a large extent (substantially) predetermined, longitudinal force. A further advantage is that the risk of material from the device, and in particular substrate 300 material, being left behind at the implantation site, is greatly reduced as the position of the separation is predetermined.

The degree of resistance during explantation is substantially determined by the dimensioning and physical properties of the one or more regions 420, 430 of configured separation resistance, as well as the selection of a suitable material.

For example, depressions may be etched, stamped, engraved, cut, punched or melted as depicted in FIG. 8. These steps may be performed during manufacturing, or later as an additional step before use. A transverse cross-section is depicted, lying in a plane comprising the first transverse axis 700 and the second transverse axis 750. As depicted, the longitudinal axis extends positively into the plane depicted (the paper) at substantially 90 degrees. The cross-section is through the distal section of the restraint, between the opening 500 and the distal edge. Three examples of regions 420 providing a predetermined resistance to the separation of the protrusion pair 401, 404 by substantially reducing the thickness (the extent along the second transverse axis 750). The reduction in thickness may be comprised in the first surface 302, in the second surface 303, or in both.

Figure 9:
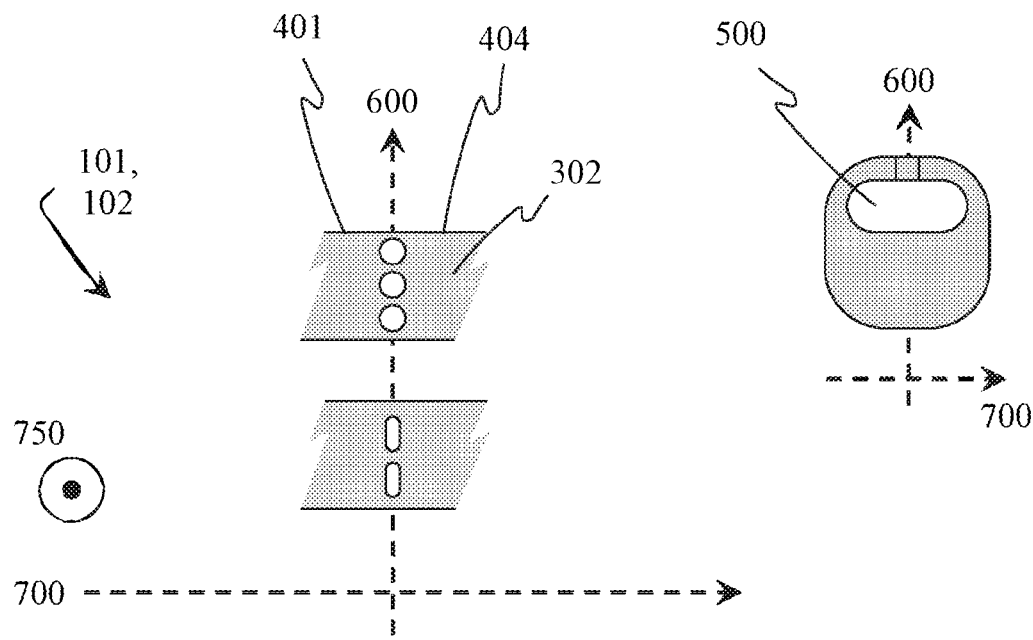
FIG. 9 depicts a zoomed view of portions of an implantable stimulation device.

Additionally or alternatively, perforations and/or serrations may be used to more accurately predetermine a position of the rupture line. These may be applied using a stamp, drill, a hot needle and/or a laser, for example. FIG. 9 depicts a zoomed view of the first surface 302 in a plane comprising the longitudinal axis 600 and the first transverse axis 700. The holes (perforations) substantially extend through the substrate, from the first surface 302 to the second surface 303—they are dimensioned too small to allow significant tissue in-growth.

In general, indentations may be used instead of holes, or in combination with holes. In addition, the thickness (extent along the second transverse axis 750) may also be modified, as depicted in FIG. 8.

Typically, with the thermoplastic polymers such as LCP, the rupture may not occur exactly along the perforations. Separation of the protrusion pair 401, 404 will occur by forces being applied to pull the protrusions apart—each connection (the bridge between the perforations or holes) between the protrusion pair 401, 404 must be separated before the protrusion pair 401, 404 can be completely separated. As the forces increase and the protrusion pair 401, 404 are separated, the cross-sections of the bridges will reduce until they are thin enough to break.

Figure 3:
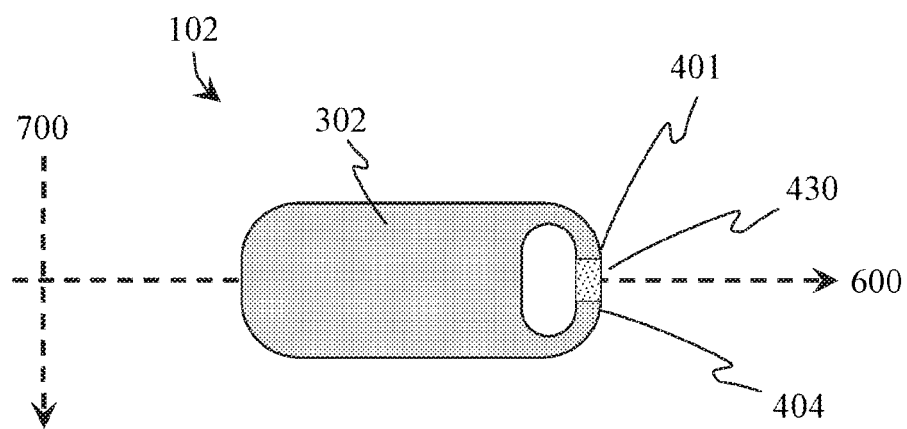
FIG. 3 depicts a third example of an implantable restraint.

FIG. 3 depicts a further modified implantable restraint 102—it is similar to the implantable restraint 101 described in relation to FIGS. 1C and 1D, except for:

a region 430, disposed between the pair of protrusions 401, 404, configured to provide a separation resistance against an increase in the separation distance of the pair of protrusions 401, 404. However, in this example, the region 430 comprises substantially different materials compared to the pair of protrusions 401, 404.

This provides a higher degree of customization, allowing the region 430 and protrusions 401, 404 to be configured in completely different ways—for example, a large difference in thickness or width—and to use materials with substantially different properties such as LCP for the protrusions 401, 404 and silicon for the region 430.

A silicon substrate may be used for the region 430 or, for example, an overmould may be used. Silicon has a tensile strength of approximately 10 MPa, so an area of 0.3 mm×0.3 mm would be required to rupture at 1N.

Parameters that determine the force required for the region 420, 430 to separate, thus separating the pair of protrusions 401, 404, include:

the transverse 700 and/or longitudinal extent 600 of the region 420, 430.
the thickness of the substrate 300, or distance between the first surface 302 and the second surface 303.
the materials comprised in the substrate 300 within the region 420, 430 and their physical properties. The separation resistance may be increased by including different materials with different tensile strengths, such as a reinforcement filament, a metal wire and/or LCP strip, or any combination thereof.
the presence of interconnecting tracks and/or interconnection layers within the region 420, 430
the presence of one or more reinforcement coatings, such as a sputtered layer of chrome.
the shape of an edge immediately proximate the one or more openings 500
the presence or shape of one or more corners in of an edge immediately proximate the one or more openings 500
the presence of one or more indentations in the first surface 302 and/or second surface 303 as depicted in FIG. 8 and FIG. 9.

As this region 420, 430 is configured to separate, it is usually a region of reduced resistance compared to the pair of protrusions 401, 404.

Typically, the longitudinal extent 600 of the region 420, 430 may be in the range 0.5 mm to 1 mm.

It may be advantageous if the force to be applied to remove the restraint 100, 101, 102 is in the range 0.5 N to 2N. Additionally, the force to be applied may be approximately 1 N.

The tensile strength of LCP is typically in the range of 100-200 MPa (N/mm$^2$).

The area (in mm$^2$) of the longitudinal cross-section through the region 420, 430 with the configured separation resistance is equal to the Force (N)/Tensile (MPa).

With a tensile strength of 100, the area configured to rupture with a force of 1N is 0.1 mm×0.1 mm. This may be effectively achieved using a high degree of perforation.

For restraints 101, 102 where a region 420, 430 of configured separation resistance is provided, this may be configured and arranged to substantially predetermine the highest force threshold that must be exceeded before explantation is possible. In other words, the anchor resistance due to the form and properties of the pair of protrusions may be configured and arranged to be substantially less—its contribution may be much lower (in some case insignificant) when compared to the embodiment of FIGS. 1A and 1B, where this anchor resistance is the major contributor to the force threshold for explantation.

If a conductive wire is used, the device may also be configured and arranged to pass sufficient current through it to melt it, similar to the way that an electrical fuse works.

Figure 2A:
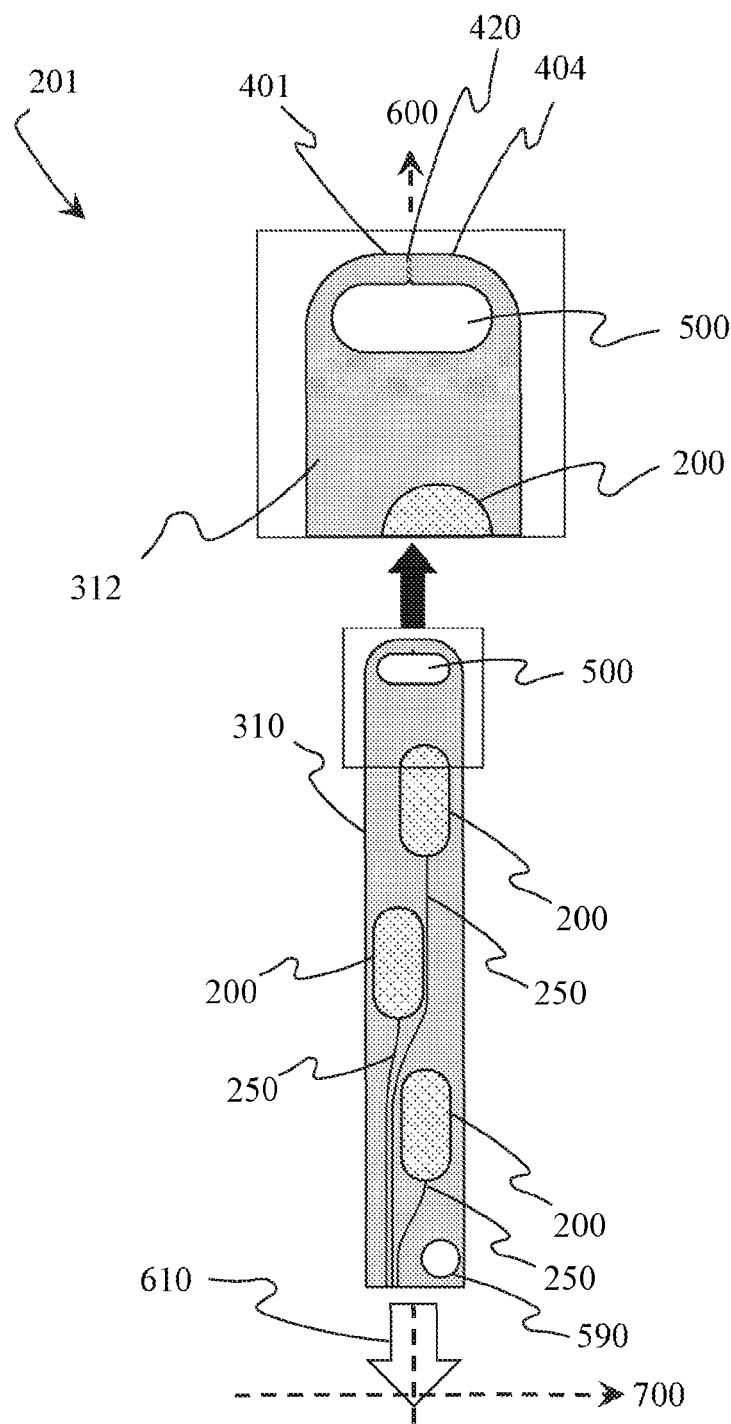
FIGS. 2A and 2B depict a first example of an implantable stimulation device.
Figure 2B:
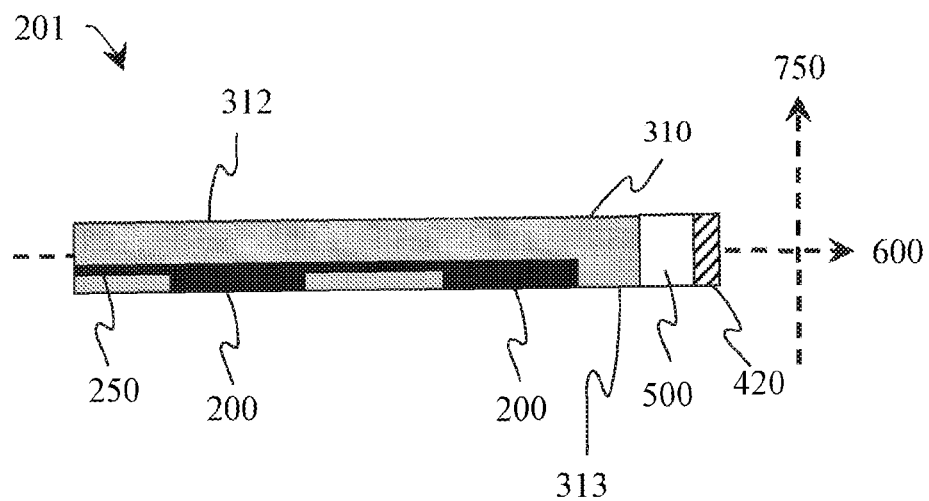

FIGS. 2A and 2B depict a first example of an implantable stimulation device 201 (or lead) comprising one or more implantable restraints 100, 101, 102 depicted above.

FIG. 2A depicts the implantable stimulation device 201 comprising:

an elongated substrate 310, disposed along a longitudinal axis 600, the substrate having a first 312 and second 313 surface disposed along substantially parallel transverse planes 600, 700. As depicted, the first surface 312 is the visible top surface, lying in the plane comprising the longitudinal axis 600 and a first transverse axis 700—the first transverse axis 700 is substantially perpendicular to the longitudinal axis 700. As depicted, this is substantially parallel to the plane of the drawing (the surface of the paper). The substrate 310 has a thickness or extent along a second transverse axis 750—this second transverse axis 750 is substantially perpendicular to both the longitudinal axis 600 and the first transverse axis 700—it is substantially perpendicular to the plane of the drawing as depicted.

As the substrate 310 may be relatively thin with a degree of flexibility, the degree to which the transverse planes 600, 700 and surfaces 312, 313 are parallel may be determined by positioning the substrate 310 on a substantially flat service.

FIG. 2B shows a transverse cross section of the implantable stimulation device depicted in FIG. 2A. It is depicted in the plane comprising the longitudinal axis 600 and the second transverse axis 750, with the longitudinal axis 600 depicted from left to right, and the second transverse axis 750 is depicted from bottom to top. Both the first 312 and second 313 surfaces are depicted as respectively an upper and lower surface. The opening 500 substantially extends through the substrate 310 between the first 312 and second surface 313.

In this embodiment 201, there is a region 420 between the protrusions 401, 404—in other words, there is a separation distance between the pair of protrusions 401, 404 across the transverse extent 700 of the region 420. In terms of the invention, the region 420 provides a (separation) resistance against an increase of the separation distance of the pair of protrusions 401, 404.

This implantable stimulation device 201 is depicted comprising an implantable restraint 101 at its distal end. Alternatively or additionally, any of the restraint variants mentioned in the description may be used, including restraints 100 and 102.

The implantable stimulation device 201 further comprises:
- one or more stimulating electrodes 200, configured to transmit energy to human or animal tissue during use (after implantation)—this may be electrical energy or another type of energy using an appropriate transducer, such as ultrasound. These may be any suitable electrode known in the art for this purpose. They are depicted in a 1-dimensional array. However, 2-d and 3-d arrays may also be used, depending on factors such as the type of tissue to be stimulated, the dimensions of the substrate 310 and the amount of room available at the implantation site. In general, the number, dimensions and/or spacings of the stimulating electrodes 200 may be selected and optimized depending on the treatment—for example, each electrode 200 may provide a separate stimulation effect, a similar stimulation effect or a selection may be made of one or two electrodes 200 proximate the tissues where the effect is to be created. The electrodes 200 may comprise a conductive material such as platinum, iridium, and/or platinum/iridium alloys and/or oxides.
- one or more electrical interconnections 250, configured to provide the one or more electrodes 200 with electrical energy. Additionally or alternatively, the substrate 310 may be a multilayer, comprising one or more electrical interconnection layers to provide the one or more electrodes 200 with electrical energy. In use, the electrical interconnections are connected to a source of electrical power (not depicted). If an LCP multilayer is used, the thickness (extent of the substrate 310 along the second transverse axis 750 or the perpendicular distance between the first surface 312 and the second surface) may be typically approximately 150 µm (micron) in the sections with no electrodes 200 or interconnections, 250 µm in the sections with an electrode 200, and 180 µm in the sections with an electrical interconnection 250. If multilayers are used, electrical interconnection layers of 25 µm (micron) may be used, for example.

The distal end of the implantable stimulation device 101 may be configured for implantation to be implanted at a different distance below the skin (different depths) or in a bodily cavity.

Although depicted as a substrate 300 with a substantially rectangular cross-section, substrates (and leads) having other cross-sections, such as square, trapezoidal may be used. The cross-section shape and/or dimensions may also vary along the longitudinal axis 600.

The device 201 may be implanted by first creating a tunnel and/or using an implantation tool.

The stimulation device 201 (comprising a restraint 101) is configured and arranged such that when a longitudinal force 610 above a predetermined threshold is applied to a proximal end, the pair of protrusions 401,404 separate by a distance approximately equal to a transverse extent 700 of the tissue anchor, such that the pair of protrusions 401, 404 moves past the tissue anchor in the direction of the longitudinal force 610.

Additionally, one or more additional openings 590 may also be provided—these are not each associated with a respective region of configured separation resistance. They are additional openings 590 which allow a small (minimum) amount of tissue growth, such that the device is secured. However, they should not be dimensioned too large as this may complicate explantation. These additional openings 590 may be used with any of the embodiments described herein. Preferably, the additional openings 590 should be have at least one extent along an axis in the range 1 to 3 mm, preferably 2 mm.

Figure 4A:
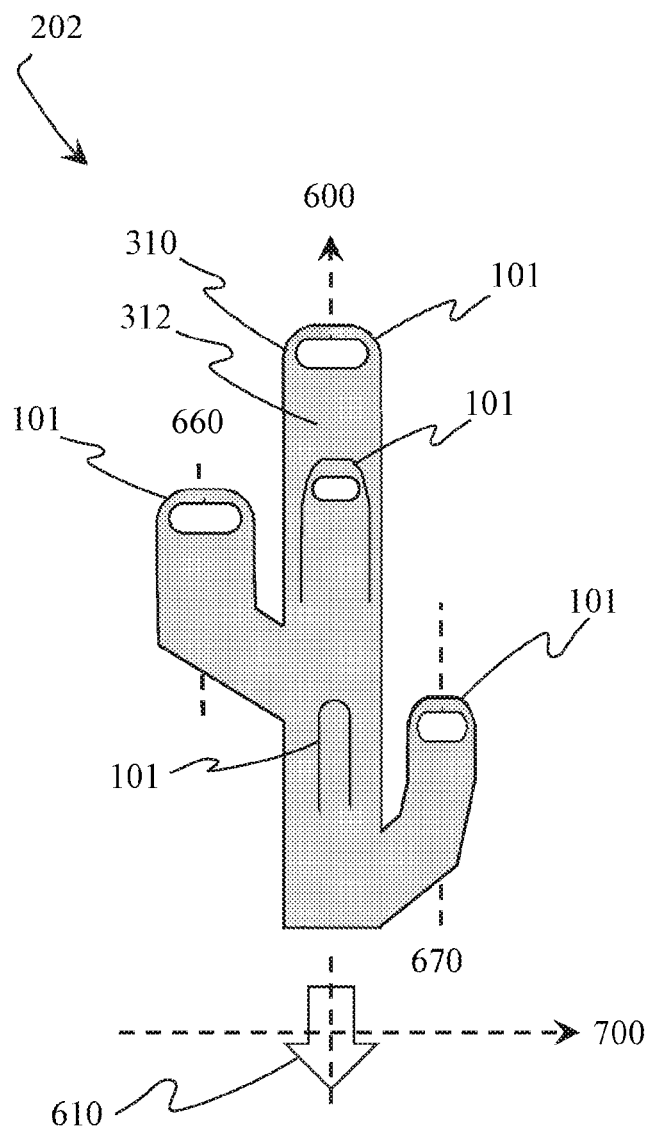
FIGS. 4A and 4B depict a second example of an implantable stimulation device.
Figure 4B:
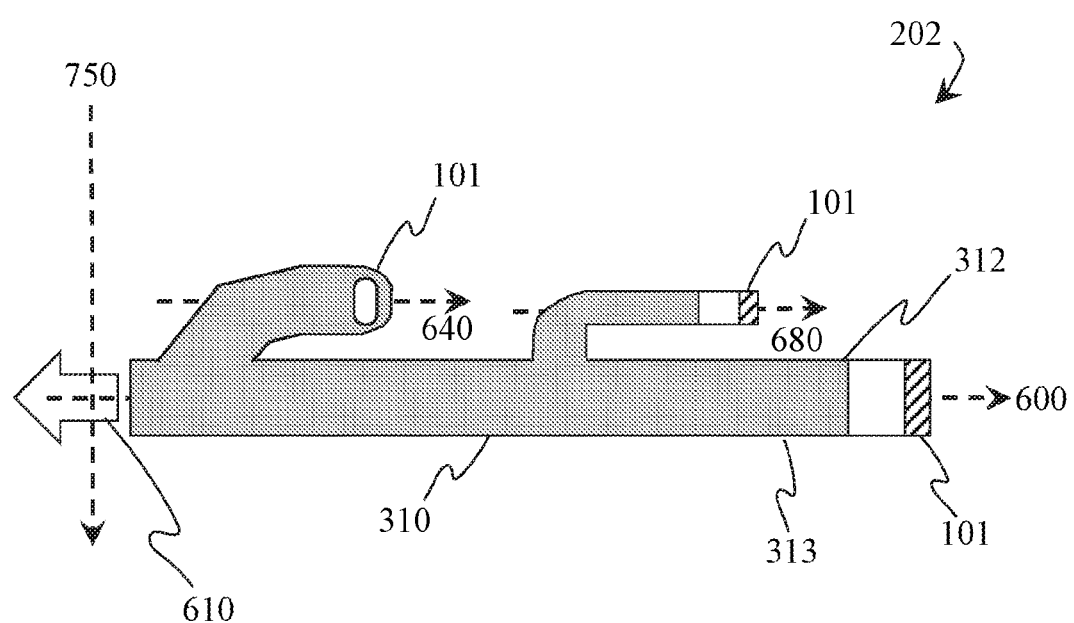

FIGS. 4A and 4B depict a second example of an improved implantable stimulation device 202—this example comprises a plurality of implantable restraints according to the invention.

FIG. 4A shows a view of the outer surface 312, which lies in a plane comprising the first transverse axis 700 and the first longitudinal axis 600. This is part of the main elongated substrate 310, which comprises an implantable restraint 101 at its distal end.

Additional restraints 101 are provided at the distal ends of additional substrates, disposed along: a second longitudinal axis 640, a third longitudinal axis 660, a fourth longitudinal axis 670, and a fifth longitudinal axis 680.

The first transverse axis 700 is substantially perpendicular to the longitudinal axes 600, 640, 660, 670, 680.

FIG. 4B shows a longitudinal cross section in the plane comprising the longitudinal axis 600 and the second transverse axis 750, wherein the second transverse axis 750 is substantially perpendicular to the longitudinal axis 600, and the second transverse axis 750 is substantially perpendicular to the first transverse axis 700.

The device 202 comprises a plurality of implantable restraints 101 at a plurality of distal ends. Alternatively or additionally, any of the restraint variants mentioned in the description may be used, including restraints 100 and 102, in any orientation.

They may comprise the same (or similar) materials or be differently configured and arranged to different degrees. They may be integrated with the (main) substrate 310 and/or attached using adhesive, heat-welding and similar.

The implantable device 202 further comprises:
electrodes and interconnections as depicted in FIG. 2A and FIG. 2B—for clarity, they have not been depicted. One or more of the restraints 101 depicted may comprise one or more electrodes, or be solely configured for fixation.

The stimulation device 202 (comprising a plurality of restraints 101) may be configured and arranged such that when a longitudinal force 610 above a predetermined threshold is applied to a proximal end, each of the pair of protrusions separate by a distance approximately equal to a transverse extent 700 of the corresponding tissue anchor, such that the pair of protrusions 401, 404 moves past the tissue anchor in the direction of the longitudinal force 610.

For each of these restraints 101, it may be predetermined that the regions of configured separation resistance rupture at the same, similar or even different force thresholds 610. When more than one restraint 101 is provided, it may also be advantageous to configure and arrange them such that they rupture by different forces—in this way, explantation may be greatly simplified, and just require a gradually increasing force to be applied for removal.

Figure 5:
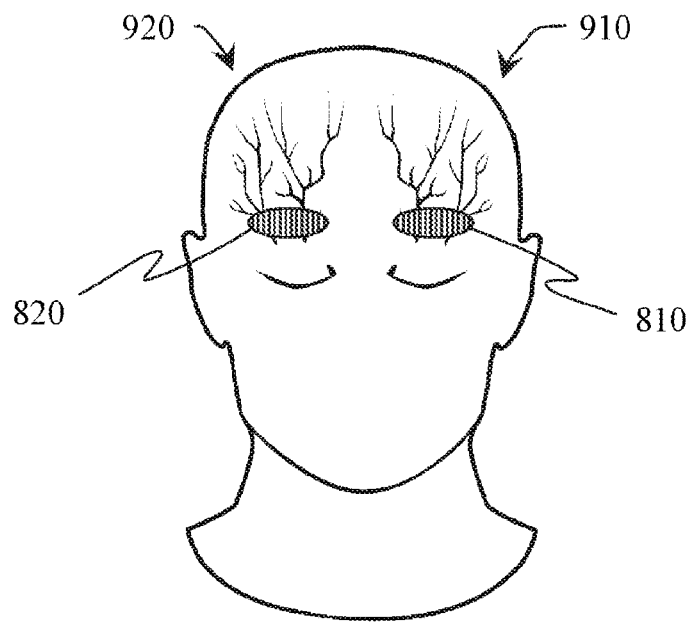
FIG. 5 and FIG. 6 depict examples of nerves that may be stimulated to treat headaches.
Figure 6:
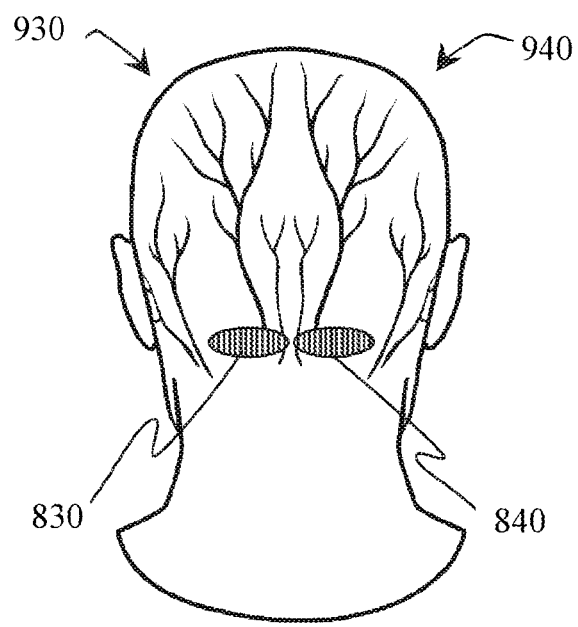

FIG. 5 and FIG. 6 depict examples of nerves that may be stimulated using a suitably configured improved implantable device 201, 202 to provide neurostimulation to treat, for example, headaches or primary headaches. The ability to secure the lead without large protrusions and/or barbs means that the comfort to the user of the implantable device 201, 202 is increased.

FIG. 5 depicts the left supraorbital nerve 910 and right supraorbital nerve 920 which may be electrically stimulated using a suitably configured device. FIG. 6 depicts the left greater occipital nerve 930 and right greater occipital nerve 940 which may also be electrically stimulated using a suitably configured device.

Depending on the size of the region to be stimulated and the dimensions of the part of the device to be implanted, a suitable location is determined to provide the electrical stimulation required for the treatment. Approximate implant locations for the distal part of the stimulation device comprising stimulation electrodes 220 are depicted as regions:

location 810 for left supraorbital stimulation and location 820 for right supraorbital stimulation for treating chronic headache such as migraine and cluster.

location 830 for left occipital stimulation and location 840 for right occipital stimulation for treating chronic headache such as migraine, cluster, and occipital neuralgia.

In many cases, these will be the approximate locations 810, 820, 830, 840 for the implantable electrode unit 201, 202.

For each implant location, 810, 820, 830, 840 a separate stimulation device 201, 202 may be used. Where implant locations 810, 820, 830, 840 are close together, or even overlapping a single stimulation device 201, 202 may be configured to stimulate at more than one implant location 810, 820, 830, 840.

A plurality of stimulation devices 201, 202 may be operated separately, simultaneously, sequentially or any combination thereof to provide the required treatment.

Figure 7:
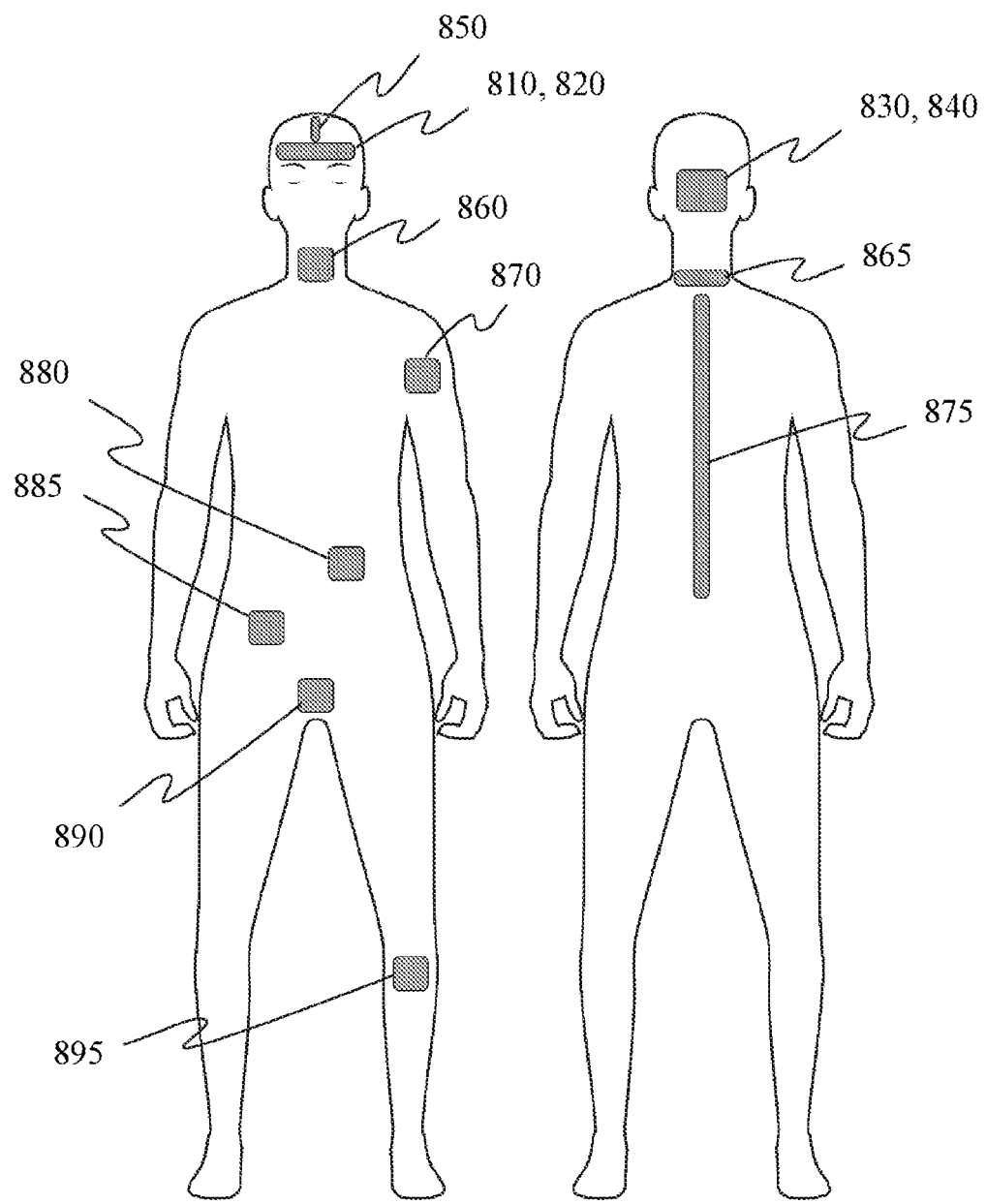
FIG. 7 depicts examples of nerves that may be stimulated for other treatments.

FIG. 7 depict further examples of nerves that may be stimulated using a suitably configured improved implantable device 201, 202 to provide neurostimulation to treat other conditions. As in FIGS. 5 and 6, the ability to be secured without large protrusions and/or barbs in these locations means that the comfort to the user of the implantable device 201, 202 is increased. The locations depicted in FIG. 5 and FIG. 6 (810, 820, 830, 840) are also depicted in FIG. 7.

Depending on the size of the region to be stimulated and the dimensions of the part of the device to be implanted, a suitable location is determined to provide the electrical stimulation required for the treatment. Approximate implant locations for the part of the stimulation device comprising stimulation electrodes are depicted as regions:

location 810 for cortical stimulation for treating epilepsy;

location 850 for deep brain stimulation for tremor control treatment in Parkinson's disease patients; treating dystonia, obesity, essential tremor, depression, epilepsy, obsessive compulsive disorder, Alzheimer's, anxiety, bulimia, tinnitus, traumatic brain injury, Tourette's, sleep disorders, autism, bipolar; and stroke recovery location 860 for vagus nerve stimulation for treating epilepsy, depression, anxiety, bulimia, obesity, tinnitus, obsessive compulsive disorder and heart failure;

location 860 for carotid artery or carotid sinus stimulation for treating hypertension;

location 860 for hypoglossal & phrenic nerve stimulation for treating sleep apnea;

location 865 for cerebral spinal cord stimulation for treating chronic neck pain;

location 870 for peripheral nerve stimulation for treating limb pain, migraines, extremity pain;

location 875 for spinal cord stimulation for treating chronic lower back pain, angina, asthma, pain in general;

location 880 for gastric stimulation for treatment of obesity, bulimia, interstitial cystitis;

location 885 for sacral & pudendal nerve stimulation for treatment of interstitial cystitis;

location 885 for sacral nerve stimulation for treatment of urinary incontinence, fecal incontinence;

location 890 for sacral neuromodulation for bladder control treatment; and location 895 for fibular nerve stimulation for treating gait or footdrop.

Other condition that may be treated include gastroesophageal reflux disease and inflammatory diseases.

Although the examples above describe the use of the embodiments of the invention in the lead for a stimulation advice, the embodiments may be used for any implantable structure that needs to be temporarily fixed well, such as an anti-conception implant.

The descriptions thereof herein should not be understood to prescribe a fixed order of performing the method steps described therein. Rather the method steps may be performed in any order that is practicable. Similarly, the examples are used to explain the algorithm, and are not intended to represent the only implementations of these algorithms—the person skilled in the art will be able to conceive many different ways to achieve the same functionality as provided by the embodiments described herein.

Although the present invention has been described in connection with specific exemplary embodiments, it should be understood that various changes, substitutions, and alterations apparent to those skilled in the art can be made to the disclosed embodiments without departing from the spirit and scope of the invention as set forth in the appended claims.

REFERENCE NUMBERS USED IN DRAWINGS 100 a first implantable restraint
101 a second implantable restraint
102 a third implantable restraint
200 one or more stimulating electrodes
201 a first implantable stimulation device (lead)
202 a second implantable stimulation device (lead)
250 one or more electrical interconnections
300 an elongated substrate (for restraint)
302 a first substantially planar surface (for restraint)
303 a second substantially planar surface (for restraint)
310 an elongated substrate (for stimulation device)
312 a first substantially planar surface (for stimulation device)
313 a second substantially planar surface (for stimulation device)
401 a first protrusion
404 a second protrusion
410 a distal opening
420 a region configured to provide a separation resistance
430 a region configured to provide a separation resistance
500 an opening
590 an additional opening
600 a (first) longitudinal axis
610 a substantially predetermined longitudinal force
640 a second longitudinal axis
660 a third longitudinal axis
670 a fourth longitudinal axis
680 a fifth longitudinal axis
700 a first transverse axis
750 a second transverse axis
810 location for left supraorbital nerve or cortical stimulation
820 location for right supraorbital stimulation
830 location for left occipital nerve stimulation 840 location for right occipital nerve stimulation
850 location for deep brain stimulation
860 location for vagus nerve, carotid artery, carotid sinus, phrenic nerve or hypoglossal stimulation
865 location for cerebral spinal cord stimulation
870 location for peripheral nerve stimulation
875 location for spinal cord stimulation
880 location for gastric stimulation
885 location for sacral & pudendal nerve stimulation
890 location for sacral neuromodulation
895 location for fibular nerve stimulation
930 left greater occipital nerve
940 right greater occipital nerve

The invention claimed is:

1. An implantable restraint comprising:
an elongated substrate, disposed along a longitudinal axis, the substrate having a first and second surface disposed along transverse planes, the substrate further comprising:
   an opening, extending through the substrate between the first and second surface, configured to receive in-growth of human or animal tissue after implantation such that a tissue anchor may form;
   a pair of facing protrusions, disposed between the opening and a distal edge of the substrate, the protrusions being configured to provide an anchor resistance against the tissue anchor to a longitudinal force applied to a proximal section of the substrate;
   wherein the pair of protrusions are further configured to separate by a distance approximately equal to a transverse extent of the tissue anchor when the longitudinal force exceeds a first predetermined threshold, such that the pair of protrusions moves past the tissue anchor in the direction of the longitudinal force;
the restraint further comprising:
   a contiguous region, disposed between the pair of protrusions and contiguous with the pair of protrusions, the contiguous region configured to provide a separation resistance against an increase in the separation distance of the pair of protrusions;
   wherein the region is further configured to rupture when the longitudinal force exceeds a second predetermined threshold, such that a distal opening is disposed between the pair of protrusions.

2. The implantable restraint according to claim 1, wherein the first predetermined threshold and/or second predetermined threshold is in the range 0.1 to 10 Newtons (N).

3. The implantable restraint according to claim 2, wherein the first predetermined threshold and/or second predetermined threshold is in the range 0.5 N to 2 N.

4. The implantable restraint according to claim 3, wherein the first predetermined threshold and/or second predetermined threshold is approximately 1 N.

5. The device according to claim 1, wherein the substrate has a width at the opening that is not greater than a width of the substrate away from the opening, when the substrate is in a relaxed position.

6. An implantable restraint comprising:
an elongated substrate, disposed along a longitudinal axis, the substrate having a first and second surface disposed along transverse planes, the substrate further comprising:
   an opening configured to receive in-growth of human or animal tissue after implantation such that a tissue anchor may form in the opening;
   a pair of protrusions, disposed between the opening and a distal edge of the substrate, the protrusions being configured to provide an anchor resistance against the tissue anchor to a longitudinal force applied to a proximal section of the substrate;
   wherein the pair of protrusions are further configured to separate by a distance approximately equal to a transverse extent of the tissue anchor when the longitudinal force exceeds a first predetermined threshold, such that the pair of protrusions moves past the tissue anchor in the direction of the longitudinal force;
the restraint further comprising:
   a region, disposed between the pair of protrusions and contiguous with the pair of protrusions, that is configured to provide a separation resistance against an increase in the separation distance of the pair of protrusions.

7. The implantable restraint according to claim 6, wherein the opening, extends through the substrate between the first and second surface.

8. The implantable restraint according to claim 6, wherein the first and second surfaces are disposed along substantially parallel transverse planes.

9. The implantable restraint according to claim 6, wherein the pair of protrusions face each other.

10. The implantable restraint according to claim 6, the restraint further comprising:
a distal opening, substantially reducing the thickness of the substrate and disposed between the pair of protrusions.

11. The implantable restraint according to claim 6, the restraint further comprising a distal opening, wherein the distal opening fully extends through the substrate and is disposed between the pair of protrusions.

12. The implantable restraint according to claim 6,
wherein the region is further configured to rupture when the longitudinal force exceeds a second predetermined threshold, such that a distal opening is disposed between the pair of protrusions.

13. The implantable restraint according to claim 12, wherein the region is contiguous.

14. The implantable restraint according to claim 12, wherein the region comprises one or more materials with a lower tensile strength than the one or more materials comprised in the protrusions.

15. The implantable restraint according to claim 6, wherein the pair of protrusions comprises a compound selected from the group consisting of: a Liquid Crystal Polymer LCP, a Polyimide, parylene, a biocompatible polymer, a biocompatible elastomer, or any combination thereof.

16. The implantable restraint according to claim 6, wherein the region and/or protrusions further comprise one or more coatings, filaments and/or wires, or any combination thereof, configured and arranged to increase the resistance of the protrusions to separate.

17. The implantable restraint according to claim 6, wherein the region and/or protrusions further comprise one or more depressions, indentations, reductions in thickness, perforations, serrations, holes, or any combination thereof, configured and arranged to at least partially predetermine the resistance of the protrusions to separate.

18. The implantable restraint according to claim 6, comprising a plurality of openings and a plurality of corresponding protrusions.

19. The device according to claim 6, wherein the anchor resistance against the tissue anchor is provided through physical contact of at least one portion of the elongated substrate along the opening.

20. An implantable stimulation device comprising:
   an elongated substrate;
   one or more stimulating electrodes, configured to transmit energy to human or animal tissue during use; and
   one or more implantable restraints according to claim 6, the restraints being attached to and/or integrated into the elongated substrate.

21. The device according to claim 20, wherein the device is used for stimulating a portion of the body selected from the group consisting of: one or more nerves, one or more muscles, one or more organs, spinal cord tissue, or any combination thereof.

22. The device according to claim 20, wherein the device is used for treatment of a condition selected from the group consisting of: headaches, primary headaches, incontinence, occipital neuralgia, sleep apnea, hypertension, gastroesophageal reflux disease, an inflammatory disease, limb pain, leg pain, back pain, lower back pain, phantom pain, chronic pain, epilepsy, an overactive bladder, post-stroke pain, obesity, or any combination thereof.

* * * * *